United States Patent [19]

O'Neal et al.

[11] Patent Number: 4,643,755

[45] Date of Patent: * Feb. 17, 1987

[54] METHOD FOR THE CONTROL OF STEM GROWTH AND STEM STIFFNESS OF GRAMINACEOUS CROPS

[75] Inventors: Thomas D. O'Neal, Princeton; Prithvi R. Bhalla, Hightstown; Barrington Cross, Rocky Hill, all of N.J.

[73] Assignee: American Cyanamid Company, Stamford, Conn.

[*] Notice: The portion of the term of this patent subsequent to Dec. 19, 1995 has been disclaimed.

[21] Appl. No.: 303,794

[22] Filed: Sep. 21, 1981

Related U.S. Application Data

[63] Continuation-in-part of Ser. No. 122,641, Feb. 19, 1981, abandoned, which is a continuation-in-part of Ser. No. 970,881, Dec. 18, 1978, abandoned, which is a continuation-in-part of Ser. No. 897,336, Feb. 21, 1978, abandoned.

[51] Int. Cl.$^4$ .............................................. A01N 33/06
[52] U.S. Cl. .......................................... 71/76; 71/103; 71/105; 71/107; 71/121; 564/112
[58] Field of Search ...................... 71/76, 121; 564/107

[56] References Cited

U.S. PATENT DOCUMENTS

| | | | |
|---|---|---|---|
| 3,356,483 | 12/1967 | Leasure et al. | 71/66 |
| 3,436,417 | 4/1969 | Strycker | 71/76 |
| 3,562,333 | 2/1971 | Schmidt-Couerus et al. | 564/107 |
| 3,672,864 | 6/1972 | Maravetz | 71/118 |
| 3,813,234 | 5/1974 | Howe | 71/76 |
| 3,844,762 | 10/1974 | Cross et al. | 71/121 |
| 3,862,833 | 1/1975 | Johnson et al. | 71/76 |
| 4,130,645 | 12/1978 | Cross et al. | 564/107 |
| 4,134,917 | 1/1979 | Ross et al. | 71/121 |
| 4,227,913 | 10/1980 | Kupelian | 71/76 |

FOREIGN PATENT DOCUMENTS

| | | | |
|---|---|---|---|
| 260647 | 3/1964 | Australia | 71/121 |
| 268075 | 1/1965 | Australia | 71/121 |

OTHER PUBLICATIONS

Templeman, "Weed Control in Perspective" (1954) Proc. Brit, W.C.C. pp. 3-11, (1954).
Jones et al., "The Relationship Between, etc", (1954), J. Sci. Food Agric. 5, pp. 38-43, (1954).

*Primary Examiner*—Glennon H. Hollrah
*Attorney, Agent, or Firm*—Estelle J. Tsevdos

[57] ABSTRACT

The invention is a novel method for the control of the relative stem growth of graminaceous crops, comprising applying to the foliage, stems, roots or seeds of said plants, or to the soil in which said plants are grown, a plant growth regulating amount of a substituted phenylnitramine.

1 Claim, No Drawings

METHOD FOR THE CONTROL OF STEM GROWTH AND STEM STIFFNESS OF GRAMINACEOUS CROPS

This application is a continuation-in-part of co-pending Ser. No. 122,641, filed Feb. 19, 1981, now abandoned which in turn is a continuation-in-part of Ser. No. 970,881 filed Dec. 18, 1978, now abandoned, which in turn is a continuation-in-part of Ser. No. 897,336 filed Feb. 21, 1978, now abandoned.

The herbicidal properties of phenylnitramines and their use for the control of weeds is described in U.S. Pat. No. 3,844,762, issued Oct. 29, 1974 (to B. Cross et al.), in which novel methods for the control of undesired plant species are disclosed by employing certain substituted phenylnitramines. The geotropic response of roots of rape and ryegrass, and the selective reduction of root growth when seeds of the plants are grown in the presence of phenylnitramines is described by R. L. Jones et al., *Journal of Science and Food Agriculture*, 5, 38 (1954). The effect of 2,4,6-tribromophenylnitramine and 2-chloro-9-fluorenol-9-carboxylic acid applied preemergence to groundsel and chickweed is described by W. Templeman, *Proceedings of the British Weed Control Conference*, 1, 3 (1954). It states that, although weed control is achieved at 11.2 and 16.8 kg/ha, these compounds possess very little selectivity and most crops, which have been examined, have also proved to be susceptible.

None of the above references even slightly suggest the novel plant growth regulating activity of substituted phenylnitramines (also known as N-nitroanilines), nor indeed could such activity be predicted therefrom.

The present invention relates to methods for the control of the relative stem growth of graminaceous crops, comprising applying to the foliage stems, roots or seeds of the plants, or to the soil in which the plants are grown, a plant growth regulating amount of a phenylnitramine or N-nitroaniline having the structure:

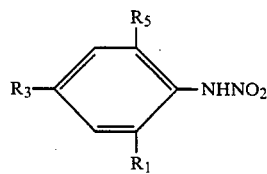

wherein $R_1$ is halogen, $C_1$–$C_4$ alkyl, $C_1$–$C_3$ haloalkyl or $C_1$–$C_3$ haloalkoxy; $R_3$ is halogen, methyl or methoxy; $R_5$ is halogen, $CF_3$, methoxy or $C_1$–$C_4$ alkyl; with the proviso that not more than two of the R groups may represent fluorine.

Preferred haloalkyl substituents are $CF_3$, $CCl_3$, $CHF_2$, $CClF_2$, $CHF_2$, $CH_2Cl$ and $CHCl_2$.

Preferred haloalkoxy substituents are $OCF_3$ and $OCHF_2$.

The term "halogen" is intended to include fluorine, chlorine, bromine and iodine.

A preferred group of compounds are those wherein $R_1$ is $CF_3$, I, Cl or Br; $R_3$ is Br, Cl or I; and $R_5$ is Cl, Br or I, provided that not more than two of said R groups may be iodine.

The above compounds are highly effective plant growth regulating agents, and are especially useful for reducing the relative stem growth and increasing the stiffness (hereinafter also referred to as dwarfing and stiffening) of the stems, of graminaceous crops, such as barley, oats, rye, wheat, sorghum, corn and rice. Usually about 0.025 to 1.5 kg/ha, and preferably 0.05 to 1.25 kg/ha of active compound, is sufficient to achieve this dwarfing and stiffening effect.

Dwarfing and/or stiffening of the stems of graminaceous crops is most advantageous to the farmer since lodging of these crops usually results in reduced yields of the affected crops.

Lodging refers to the deflection of the plant from the vertical, varying in degree from only a slight deflection to complete deflection (i.e. plants prone) caused by, in most cases, the action of wind and/or rain on the plants. This deflection is such that when the causal agent (wind, rain) is no longer present, the deflection is neither immediately nor completely overcome. Moreover, where extensive or severe lodging has occurred, the crop may be difficult to harvest and the yield markedly reduced.

Inasmuch as the compounds of the invention have only limited solubility in water, they are generally formulated for foliar application as wettable powders, flowable dispersions or emulsion concentrates, which are usually dispersed in water or in other, inexpensive, liquid diluents for application to the foliage of the plants as a liquid spray. However, when the compounds are to be used where soil treatments are involved, they may also be formulated as granular products.

A typical wettable powder can be prepared by grinding together approximately 46% by weight of a finely divided carrier such as attapulgite, 50% by weight of the phenylnitramine compound, 3% by weight of the sodium salt of condensed naphthalene sulfonic acids and 1% by weight of sodium N-methyl-N-oleoyltaurate.

A typical flowable dispersion can be prepared by admixing about 42% by weight of the phenylnitramine with about 3% by weight of the sodium salt of condensed naphthalene sulfonic acids, 2% by weight of finely divided bentonite and 53% by weight of water.

Emulsion concentrates may be prepared by dissolving 15% to 70% by weight of the compound in 85% to 30% of a solvent such as benzene, toluene, xylene, kerosene, 2-methoxy ethanol, propylene glycol, diethylene glycol, diethylene glycol monomethyl ether, formamide, methylformamide, and the like, and mixtures thereof. Advantageously, surfactants such as polyoxyethylated vegetable oil or an alkyl phenoxy polyoxyethylene ethanol are also incorporated in amounts of 1% to 5% by weight of the concentrate.

A granular product can be prepared by dissolving the compound in a suitable solvent, such as acetone, and spraying the resultant solution on a granular carrier such as sand, silica, kaolin, corn cob grits, and the like.

In accordance with this invention, the phenylnitramines can be prepared from the corresponding substituted anilines by a variety of conventional procedures. For illustrative purposes, on such procedure is hereinbelow graphically illustrated and described as follows:

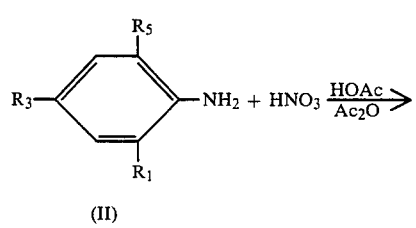

(II)

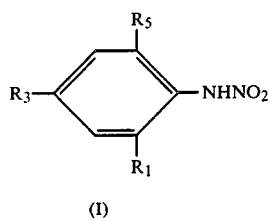

(I)

wherein $R_1$, $R_3$ and $R_5$ are as hereinabove defined. The above synthesis is conveniently carried out in a solvent, such as acetic acid, preferably in the presence of a dehydrating agent, such as acetic anhydride. The product may be precipitated from the reaction mixture by the addition of ice water. Purification may be effected by conventional procedures such as recrystallization, chromatography, and the like.

The phenylnitramines, wherein $R_1$ and/or $R_5$ are haloalkyl or hydroxyalkyl and $R_3$ is halogen, can be prepared by a two-step synthesis involving Step 1, the reaction of the appropriate haloalkyl aniline or haloalkoxyaniline with halogen (e.g. chlorine or bromine) in the presence of an acid acceptor such as sodium acetate, potassium acetate, or the like, in the presence of an inert organic solvent (e.g. tert-butanol, $CCl_4$, ethylene dichloride, chlorobenzene, or the like). The reaction is generally conducted at a temperature in the range of from 25° C. to 75° C., and preferably at a temperature of about 45° C. to 55° C. The reaction yields the corresponding 2,4,6-trisubstituted aniline, which may then be converted, in Step 2, to the corresponding 2,4,6-trisubstituted phenylnitramine by reaction with nitric acid in the presence of a solvent, such as acetic acid, and a dehydrating agent, such as acetic anyhydride. Steps 1 and 2 can be graphically illustrated as follows:

Step 1

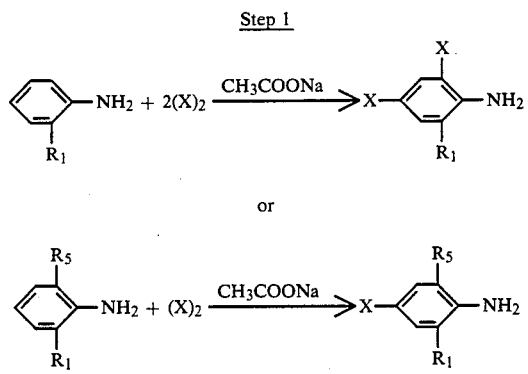

wherein $R_1$ and $R_5$ are haloalkyl or haloalkoxy, and X is chlorine or bromine.

Step 2

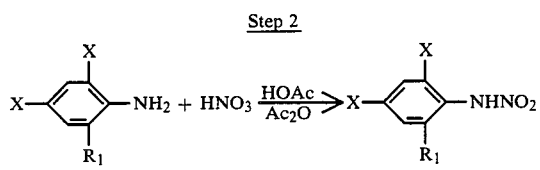

-continued
Step 2

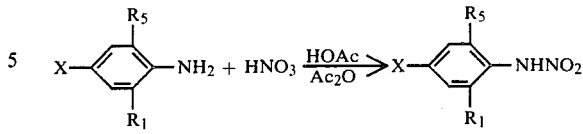

wherein $R_1$, $R_5$ and X are as described above.

Among the compounds of the invention which are particularly effective for inhibiting lodging of graminaceous crops are:
2,4,6-tribromo-N-nitroaniline;
4-chloro-2,6-diiodo-N-nitroaniline;
2,4-dibromo-6-iodo-N-nitroaniline;
2,6-dibromo-4-chloro-N-nitroaniline;
2,6-dichloro-4-iodo-N-nitroaniline;
2,4-dibromo-α,α,α-trifluoro-N-nitro-o-toluidine;
2-bromo-4-chloro-6-iodo-N-nitroaniline;
4-bromo-2-chloro-6-iodo-N-nitroaniline;
2-chloro-4,6-diiodo-N-nitroaniline;
2,4-dibromo-6-chloro-N-nitroaniline;
2,6-dibromo-4-iodo-N-nitroaniline;
4-bromo-2,6-diiodo-N-nitroaniline;
4-bromo-N-nitro-2,6-xylidine;
4-bromo-2,6-dichloro-N-nitroaniline;
2-bromo-4,6-diiodo-N-nitroaniline;
2,6-dibromo-N-nitro-p-anisidine;
2,4,6-trichloro-N-nitroaniline;
2,4-dibromo-6-α,α-difluoro-N-nitro-o-toluidine;
2,4-dibromo-6-α,α,α-trichloro-N-nitro-o-toluidine;
2,4-dibromo-6-α,α-dichloro-N-nitro-o-toluidine;
2,4-dichloro-6-α,α,α-trifluoro-N-nitro-o-toluidine;
4-bromo-2,6-α,α,α-ditrifluoro-N-nitro-2,6-xylidine;
2,4-dibromo-6-α,α,α-trifluoro-N-nitro-o-anisidine;
2,4-dibromo-6-α-fluoro-N-nitro-o-toluidine;
2,4-dibromo-6-α-chloro-N-nitro-o-toluidine;
2-nitramino-3,5-dibromobenzoic acid, methyl ester;
2,nitramino-3,5-dibromobenzonitrile;
2,4-dibromo-6-methylsulfonyl-N-nitroaniline;
2,4-dibromo-6-α,α-difluoro-N-nitro-o-anisidine;
2-nitramino-4,6-dibromobenzenesulfonyl fluoride;
2,6-dibromo-2-nitro-N-nitroaniline;
2,6-dibromo-4-fluoro-N-nitroaniline;
2-bromo-2,6-difluoro-N-nitroaniline;
2,4-dibromo-6-isopropyl-N-nitroaniline; and
2-bromo-4,6-dichloro-N-nitroaniline.

This invention is further illustrated by examples set forth below.

EXAMPLE 1

General Procedure for the Preparation of Phenylnitramines

To a cooled (10° C. to 20° C.) solution containing an appropriately substituted aniline (0.10 mole) in glacial acetic acid (100 to 500 ml) is added dropwise, with cooling and stirring during 15 to 30 minutes, 90% nitric acid (15 to 16 ml; 0.28–0.30 mole). In many reactions, the nitrate salt precipitates out. After 15 minutes to one hour, acetic anhydride (15 ml) is added dropwise with stirring and the temperature allowed to attain 18° C. to 25° C. The reaction mixture darkens and becomes homogeneous, at which point the mixture is poured into ice water (1:1, 1 liter). The resulting precipitate is filtered, washed with water and dissolved in aqueous 10% sodium carbonate.

The acidic filtrate is extracted with chloroform (2×200 ml), and the chloroform layer is washed with water (2×200 ml). The chloroform layer is extracted with 10% aqueous sodium carbonate, and both of the above carbonate solutions are combined, washed with chloroform, cooled to 10° C., and acidified with ice-cold 2N hydrochloric acid to precipitate the phenylnitramine product. The nitramine is filtered, washed with cold water, dried in vacuo and recrystallized from the appropriate solvent.

If desired, the above chloroform solution may be evaporated to dryness to afford a mixture of the desired product, the unreacted aniline and side products. The impurities may be separated by conventional procedures, such as selective crystallization extraction, chromatography, and the like.

Various substituted phenylnitramines prepared by the above general procedure are set forth in Table I.

TABLE I

| $R_{(n)}$ | Melting Point °C. | Crystallization Solvent | % Yield |
|---|---|---|---|
| 2,4,6-tri-Br | 138–139 dec. | cyclohexane | 38 |
| 2,4,6-tri-Cl | 138 dec. | cyclohexane | 27 |
| 2-Cl; 6-Br; 4-I | 131–133 dec. | hexane | 77 |
| 2,6-di-Cl; 4-Br | 139–140 dec. | hexane | 64 |
| 2-Br; 4,6-di-F | 96–98 dec. | hexane | 67 |
| 2,6-di-I; 4-Br | 124–127 dec. | hexane | 50 |
| 2,6-di-CH$_3$; 4-Br | 129–131 dec. | hexane | 20 |
| 2,6-di-I; 4-Cl | 128–131 dec. | hexane | 43 |
| 2,6-di-Br; 4-Cl | 132–134 dec. | hexane | 67 |
| 2,6-di-Br; 4-F | 105–107 dec. | hexane | 63 |
| 2,6-di-Br; 4-I | 131–133 dec. | hexane | 27 |
| 2,4-di-Br; 6-I | 121–123 dec. | hexane | 44 |
| 2,4-di-Br; 6-i-CH(CH$_3$)$_2$ | 93–94 dec. | hexane | 20 |
| 2,4-di-Br; 6-CH$_3$ | 106–108 dec. | hexane | 76 |
| 2,6-di-Cl; 4-I | 128–130 dec. | hexane | 33 |
| 2,4-di-Cl; 6-I | 119–122 dec. | hexane | 45 |
| 2,6-di-I; 4-F | 124–125 | hexane | 55 |
| 2,4,6-tri-I | 140–142 | hexane | 76 |
| 2,4-di-Br; 6-Cl | 137 | hexane | 30 |
| 2,4-di-Cl; 6-Br | 136 | hexane | 73 |
| 2,4-di-I; 6-Cl | 118.5–120 | hexane | 28 |
| 2,4-di-I; 6-Br | 120.5–121 | hexane | 21 |
| 2,6-di-Cl; 6-CH$_3$ | 122–123 | hexane | 32 |
| 2,4-di-CH$_3$; 6-Br | 104.5–106 | hexane | 25 |
| 2-I; 4-Cl—6-Br | 121–123 | hexane | 50 |
| 2-I; 4-Br—6-Cl | 131–133 | hexane | 50 |
| 2,4-di-Br; 6-CF$_3$ | 126–128 | hexane | 40 |

EXAMPLE 2

Preparation of 2-Bromo-4-chloro-6-iodo-N-nitroaniline

To an ice-cooled solution of 2-bromo-4-chloro-6-iodoaniline (18.05 mmole, 6.0 g) in 200 ml of glacial acetic acid is added dropwise, 90% nitric acid (173.52 mmole, 8.1 ml). The precipitated salt is observed, while continued stirring with cooling for 0.5 hour. Acetic anhydride (8.1 ml) is added dropwise with cooling. The solution darkens and becomes homogeneous. The cooled solution is poured into 600 ml of ice water, the precipitate is filtered, washed with water, then dissolved in 10% sodium bicarbonate (300 ml). The filtrate is extracted with methylene chloride (3×100 ml), and the combined methylene chloride extracts are washed with water (3×100 ml). The methylene chloride layer is extracted with 10% sodium bicarbonate (3×100 ml), and both of the bicarbonate solutions are combined, then washed with methylene chloride until the bicarbonate layer is colorless. The bicarbonate solution is cooled in an ice bath, then acidified with 15% HCl. The precipitated product is filtered, washed with water, then dried in vacuo. Recrystallization from hot hexane yield 4.22 g of product melting at 121°–123° C.(dec.).

EXAMPLE 3

Preparation of 4-Bromo-2,6-dimethyl-N-nitroaniline

To a cooled (−60° C.) solution of 4-bromo-2,6-dimethylaniline (0.037 mole, 7.4 g) dissolved in anhydrous ether (100 ml) under nitrogen with stirring is added dropwise, phenyl lithium (21.5 ml, 0.040 mole). The solution is stirred for 1.5 hours at −60° C. The solution is allowed to warm to −10° C., then it is cooled to −60° C. The nitrogen flow is stopped while methyl nitrate (0.044 mole, 3.5 g) in anhydrous ether (25 ml) is added dropwise. The solution is stirred for 0.5 hour at −60° C., then it is allowed to warm to room temperature. The solution is stirred for 1.6 hours; the ether layer is evaporated. The solid is dissolved in water (250 ml), then is extracted with ether (2×100 ml). The cold water layer is acidified with 5% HCl. The precipitated product is filtered, washed with water, and dried in vacuo. Recrystallization from hot hexane yields 2.5 g of the desired product melting at 129°–131° C.

EXAMPLE 4

Preparation of 2-Trifluoromethyl-4,6-dibromoaniline

To a solution of 2-trifluoromethylaniline (62.06 mmole, 10.0 g) and sodium acetate (155.17 mmole, 12.73 g) in 335 ml tert-butanol is added dropwise, a solution of bromine (124.13 mmole, 6.8 ml) in 65 ml tert-butanol. The reaction mixture is warmed to 50° C. for 0.5 hour during which the solution becomes colorless. The solution is poured into water, then is extracted with ether (3×100 ml). The combination ether extracts are washed with water (2×200 ml), saturated sodium chloride (2×200 ml), and water (3×200 ml). The ether layer is dried over MgSO$_4$, filtered, then evaporated at reduced pressure to give an oil, which upon treatment with petroleum ether (30°–60° C.) yields a solid. Recrystallization from 95% ethanol and water yields 11.3 g of product melting at 42°–44° C.

EXAMPLE 5

Preparation of 2-Trifluoromethyl-4,6-dibromo-N-nitroaniline

To an ice-cooled solution of 2-trifluoromethylacetic acid is added dropwise, 90% nitric acid (181.15 mmole, 8.4 ml). Continued stirring with cooling for 0.5 hour. Acetic anhydride (8.4 ml) is added dropwise with cooling. After the addition is complete, the mixture is allowed to warm to 25° C. during which the solution darkens and becomes homogeneous. The solution is poured into 600 ml of ice water, the precipitated product is filtered, washed with water, then dissolved in 10% sodium bicarbonate (300 ml). The filtrate is extracted with methylene chloride (3×100 ml), and the combined methylene chloride extracts are washed with water (3×100 ml). The methylene chloride layer is extracted with 10% sodium bicarbonate (3×100 ml), and both of the bicarbonate solutions are combined, then washed with methylene chloride (5×100 ml). The bicarbonate solution is cooled in an ice bath, then acidified with 15% HCl. The precipitated product is filtered, washed with water, then dried in vacuo. Recrystallization from hot hexane yields 3.92 g of product melting at 126°–128° C. (dec).

EXAMPLE 6

Evaluation of the Dwarfing and Stiffening Effect of the Phenylnitramines of the Present Invention on Barley In the following tests, the appropriate phenylnitramines are dissolved or dispersed in acetone-water (1:1) mixtures at the final concentration corresponding to the kg/ha rates indicated in the tables below. The solutions also contain 0.1% to 0.25% v/v colloidal BIOFILM ® (a product of Colloidal Products Corp.) which is a mixture of alkyl aryl polyethoxyethanol, free and combined fatty acids, glycol ethers, dialkylbenzene carboxylate and 2-propanol.

The plant species used in these tests are barley (*Hordeum vulgare* var. Villa and var. Larker), wheat (*Triticum aestivum* var. Era and var. Garnet), and rice (*Oryza sativa* var. Saturn).

The solution or dispersion of the compound under test is sprayed at a rate of 747 l/ha with a moving nozzle over a stationary track. The spray nozzle moves at a constant speed over the test species.

In the preemergence tests, containers are filled to within 2.5 cm of the top with greenhouse potting soil, seeds are added, covered with additional potting soil, and then sprayed. The pots were watered immediately before treatment and benched at random in the greenhouse. Normal watering and fertilizing practices are followed (pesticides are applied to the plants as needed). Minimum day and night temperatures of 18.3° C. are maintained during cooler periods of the year. Normal daily fluctuations occur during the summer season.

Postemergence tests are conducted in like manner to the preemergence tests. However, the plant species employed in these tests are well established seedlings 10 to 20 cm in height. Plants are watered prior to treatment and are sprayed to provide the kg/ha rates indicated in the tables below.

Data Recording

Periodic observations are made after treatment and morphological changes are noted. At the time of observation, the height of plants is determined. If the plants are maintained to maturity and harvested, second internode lengths and second internode diameters are also determined. From these measurements, as compared to the untreated controls, the dwarfing effect of the instant compounds on barley can be determined.

Measurement of Culm (Stem) Stiffness

Six to eight plants, forming a straight row, are pulled over to an angle of approximately 45° off vertical with a spring balance attached through a loop of string encircling the line of plants directly below the top. The force required to pull the plants over is read off the spring balance and is given in grams.

At each level of active compound, the treatments are replicated, as are the controls. In the following tables, the phenylnitramines tested at the indicated kg/ha rates are listed together with the averaged data of the corresponding replicates.

TABLE II

Evaluation of the dwarfing effect of phenylnitramines on barley (var. Villa) applied as a preemergence spray. The barley seeds are planted in 12.5 cm pots in greenhouse soil. Five replicates are used for each treatment and for the untreated controls. Height measurements are taken 15 days post-treatment. At each kg/ha rate, the data of the corresponding replicates are averaged.

| Compound | Rate: kg/ha | Height in cm | Height Reduction in % |
|---|---|---|---|
| Control | — | 19.4 | — |
| 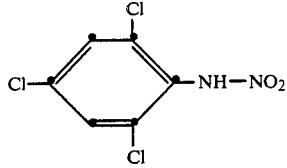 | 0.56 | 19.4 | — |
| | 1.12 | 17.0 | 12.4 |
| | 2.24 | 21.2 | — |

TABLE III

Evaluation of the dwarfing effect of phenylnitramines on barley (var. Villa) applied as a postemergence spray when the plants are 15 cm tall. Five replicates are used for each treatment and for the untreated controls. Measurements are taken 3 weeks post-treatment. At each kg/ha rate, the data of the corresponding replicates are averaged.

| Compound | Rate: kg/ha | Height in cm | Height Reduction in % |
|---|---|---|---|
| Control | — | 31.4 | — |
| 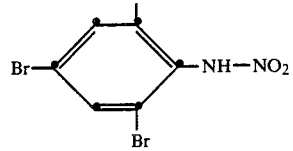 | 0.28 | 24.8 | 21.1 |
| | 0.56 | 21.2 | 32.5 |
| | 1.12 | 20.0 | 36.3 |

TABLE IV

Evaluation of the dwarfing effect of phenylnitramines on barley (var. Larker) applied as a postemergence spray when the plants are one week old. Five replicates are used for each treatment and eleven replicates are used for untreated controls. Measurements are taken 16 days post-treatment. At each kg/ha rate, the data of the corresponding replicates are averaged.

| Compound | Rate: kg/ha | Height in cm | Height Reduction in % |
|---|---|---|---|
| Control | — | 30.9 | — |
| 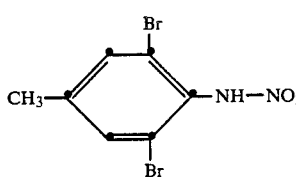 | 0.56 | 26.8 | 13.2 |
| | 0.84 | 25.0 | 19.0 |
| | 1.12 | 23.4 | 24.2 |
| | 1.68 | 24.4 | 21.0 |
| | 0.56 | 28.8 | 6.8 |
| | 0.84 | 28.2 | 8.7 |
| | 1.12 | 29.6 | 4.2 |
| | 1.68 | 30.5 | 1.2 |

TABLE IV-continued

Evaluation of the dwarfing effect of phenylnitramines on barley (var. Larker) applied as a postemergence spray when the plants are one week old. Five replicates are used for each treatment and eleven replicates are used for untreated controls. Measurements are taken 16 days post-treatment. At each kg/ha rate, the data of the corresponding replicates are averaged.

| Compound | Rate: kg/ha | Height in cm | Height Reduction in % |
|---|---|---|---|
| 2,4,6-trimethylphenyl-NH—NO$_2$ | 0.56 | 28.4 | 8.1 |
| | 0.84 | 21.2 | 31.3 |
| | 1.12 | 28.2 | 8.7 |
| | 1.68 | 31.0 | — |

TABLE V

Evaluation of the dwarfing effect of phenylnitramines on barley (var. Conquest) applied as a postemergence spray when the plants are 10 days old. Four replicates are used for each treatment. The plants are maintained under greenhouse conditions and are exposed to high intensity metal halide lights for a photo-period of 16 hours daily. Measurements are taken 3 weeks post-treatment. At each kg/ha rate the data of the corresponding replicates are averaged.

| Compound | Rate: kg/ha | Height in cm | Height Reduction in % |
|---|---|---|---|
| Control | — | 48.5 | — |
| 2,4,6-tribromophenyl-NH—NO$_2$ | 0.25 | 41.8 | 13.8 |
| | 0.50 | 37.8 | 22.1 |
| | 0.75 | 35.2 | 27.4 |

TABLE VI

Evaluation of the dwarfing and stiffening effect of 2,4,6-tribromo-N—nitroaniline on barley (var. Larker) applied as a preemergence spray. The seeds are planted in 17.5 cm pots in greenhouse potting soil. Five replicates are used for each treatment and for untreated controls. Measurements are taken on weeks indicated post-treatment. At each kg/ha rate, the data of the corresponding replicates are averaged. The plants are maintained during the test under greenhouse conditions, and are exposed to high intensity metal halide lights for a photo-period of 19 hours daily.

| Compound | Rate: kg/ha | Height in cm | Height Reduction in % | Stiffness in g | % Change in Stiffness |
|---|---|---|---|---|---|
| | | 7 Weeks | | | |
| Control | — | 64.8 | — | 75 | — |
| 2,4,6-tribromophenyl-NH—NO$_2$ | 0.28 | 55.2 | 14.8 | 125 | 66 |
| | 0.56 | 51.8 | 20.7 | 185 | 146 |
| | 1.12 | 54.6 | 15.7 | 160 | 113 |
| | | 9 Weeks | | | |
| Control | — | 65.4 | — | 135 | — |
| 2,4,6-tribromophenyl-NH—NO$_2$ | 0.28 | 56.2 | 14.0 | 280 | 107 |
| | 0.56 | 51.4 | 21.4 | 285 | 111 |
| | 1.12 | 54.2 | 17.1 | 365 | 170 |
| | | 13 Weeks | | | |
| Control | — | 60.4 | — | | |
| 2,4,6-tribromophenyl-NH—NO$_2$ | 0.28 | 53.8 | 10.9 | | |
| | 0.56 | 51.2 | 15.2 | | |
| | 1.12 | 55.2 | 8.6 | | |

TABLES VIIA, VIIB, VIIC AND VIID

Dwarfing and stiffening effects of 2,4,6-tribromo-N-nitroaniline on barley (var. Larker) are evaluated using a postemergence spray at various stages of plant development as indicated in the following tables. The seeds are planted in 17.5 cm pots in greenhouse potting soil.

Five replicates are used for each treatment and for the untreated controls at each stage. The plants are maintained under greenhouse conditions and are exposed to high intensity metal halide lamps for a photo-period of 19 hours daily. Measurements are taken on days indicated posttreatment. At each kg/ha rate, the data of the corresponding replicates are averaged.

TABLE VIIA

Stage 1.
The plants are treated 12 days after planting when they are 10–11 cm tall and had 3 leaves.

| Compound | Rate: kg/ha | Height in cm | Height Reduction in % |
|---|---|---|---|
| | | 10 Days | |
| Control | — | 26.4 | — |
| 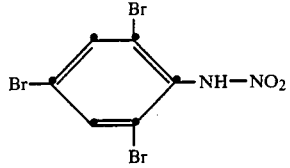 (2,4-dibromo-NH—NO2) | 0.28 | 16.2 | 38.6 |
| | 0.56 | 19.6 | 25.7 |
| | 1.12 | 20.0 | 24.2 |
| | | 23 Days | |
| Control | — | 45.0 | — |
| 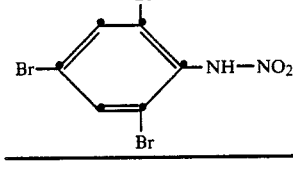 | 0.28 | 43.2 | 4.0 |
| | 0.56 | 40.5 | 10.0 |
| | 1.12 | * | |
| | | 35 Days | |
| Control | — | 51.7 | — |

TABLE VIIA-continued

Stage 1.
The plants are treated 12 days after planting when they are 10–11 cm tall and had 3 leaves.

| Compound | Rate: kg/ha | Height in cm | Height Reduction in % |
|---|---|---|---|
| 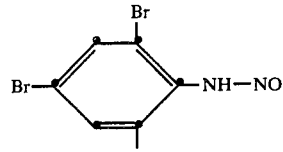 | 0.28 | 55.7 | — |
| | 0.56 | 55.7 | — |
| | 1.12 | | |
| | | 43 Days | |
| Control | — | 57.0 | — |
| 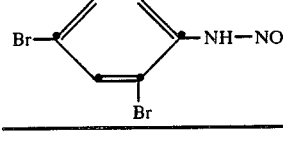 | 0.28 | 60.0 | — |
| | 0.56 | 53.8 | 5.6 |
| | 1.12 | | |
| | | 49 Days | |
| Control | — | 48.3 | — |
| 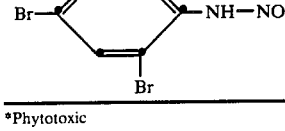 | 0.28 | 52.3 | — |
| | 0.56 | 54.5 | — |
| | 1.12 | | |

*Phytotoxic

TABLE VIIB

Stage 2.
The plants are treated 25 days after planting, when they are 30 cm tall, have 3–4 leaves and 2 internodes.

| Compound | Rate: kg/ha | 10 Days | | 40 Days | | 50 Days | |
|---|---|---|---|---|---|---|---|
| | | Height in cm | Height Reduction in % | Height in cm | Height Reduction in % | Height in cm | Height Reduction in % |
| Control | — | 54.6 | — | 61.0 | — | 57.8 | — |
| 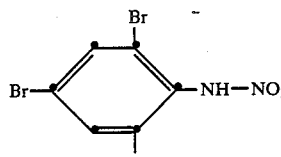 | 0.28 | 54.2 | 0.7 | 54.8 | 10.1 | 54.6 | 5.5 |
| | 0.56 | 50.8 | 6.9 | 59.2 | 2.9 | 53.4 | 7.6 |
| | 1.12 | 49.2 | 9.8 | 58.0 | 4.9 | 52.6 | 8.9 |

TABLE VIIC

Stage 3.
The plants are treated 35 days after planting, when they are 50 cm tall, have 4–5 leaves and 4 internodes.

| Compound | Rate: kg/ha | 12 Days | | 30 Days | | 40 Days | |
|---|---|---|---|---|---|---|---|
| | | Height in cm | Height Reduction in % | Height in cm | Height Reduction in % | Height in cm | Height Reduction in % |
| Control | — | 59.3 | — | 62.0 | — | 56.3 | — |

TABLE VIIC-continued

Stage 3.
The plants are treated 35 days after planting, when they are 50 cm tall, have 4-5 leaves and 4 internodes.

| Compound | Rate: kg/ha | 12 Days Height in cm | 12 Days Height Reduction in % | 30 Days Height in cm | 30 Days Height Reduction in % | 40 Days Height in cm | 40 Days Height Reduction in % |
|---|---|---|---|---|---|---|---|
| 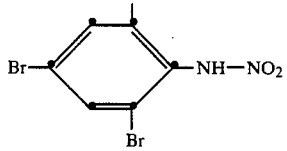 | 0.28 | 56.4 | 4.8 | 58.8 | 5.1 | 52.0 | 8.3 |
| | 0.56 | 58.2 | 1.8 | 60.6 | 2.2 | 56.4 | — |
| | 1.12 | 57.0 | 3.8 | 58.2 | 6.1 | 56.0 | — |

TABLE VIID

The stem stiffening effect of 2,4,6-tribromo-N—nitroaniline applied as a postemergence spray on barley (var. Larker) at three stages of development of said plants is summarized as the average of 5 replicates at each kg/ha rate of application.

| Compound | Rate: kg/ha | Stage 1 35 Days ST | Stage 1 35 Days % ST | Stage 1 50 Days ST | Stage 1 50 Days % ST | Stage 2 22 Days ST | Stage 2 22 Days % ST | Stage 2 40 Days ST | Stage 2 40 Days % ST | Stage 3 12 Days ST | Stage 3 12 Days % ST | Stage 3 30 Days ST | Stage 3 30 Days % ST |
|---|---|---|---|---|---|---|---|---|---|---|---|---|---|
| Control | — | 281.2 | — | 218 | — | 202 | — | 180 | — | 205 | — | 233 | — |
| 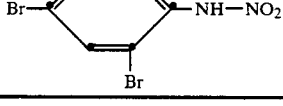 | 0.28 | 303 | 7.8 | 235 | 7.8 | 262 | 27 | 231 | 28 | 187 | — | 181 | — |
| | 0.56 | 262 | — | 215 | — | 250 | 21.9 | 265 | 47 | 237 | 15.6 | 268 | 15 |
| | 1.12 | — | — | 269 | 23.4 | 292 | 42.4 | 241 | 33.8 | 233 | 13.6 | 222 | — |

ST = Stiffening (force in grams).
% ST = Percent increase in stem stiffness relative for checks.

TABLE VIII

Evaluation of the dwarfing effect of phenylnitramines on wheat (var. Era and var. Garnet) and on rice (var. Saturn) applied as preemergence spray. Six replicates are used for each treatment and for untreated controls. Measurements are taken 19 days post-treatment. At each kg/ha rate, the data of the corresponding replicates are averaged.

| Compound | Rate: kg/ha | Wheat var. Era Height in cm | Wheat var. Era Height Reduction in % | Wheat var. Garnet Height in cm | Wheat var. Garnet Height Reduction in % | Rice var. Saturn Height in cm | Rice var. Saturn Height Reduction in % | Remarks |
|---|---|---|---|---|---|---|---|---|
| Control | — | 32.0 | — | 34.25 | — | 30.4 | — | |
| 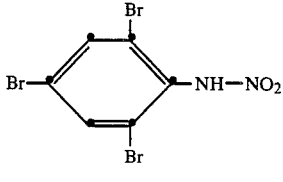 | 0.56 | 30.5 | 4.7 | 30.8 | 10.1 | 25.5 | 16.1 | Very slight tip burn on rice. |
| | 1.12 | 29.5 | 7.8 | 30.5 | 10.9 | 23.6 | 23.4 | Slight tip burn on rice. |
| | 1.68 | 29.2 | 8.8 | 28.4 | 17.1 | 16.3 | 46.4 | Approximately 25% stand reduction and moderate tip burn on rice. |
| | 2.24 | 28.0 | 12.5 | 27.4 | 20.0 | 16.0 | 47.4 | Approximately 50% stand reduction and severe tip burn on rice. |

TABLE IX

Evaluation of the dwarfing effect of phenylnitramines on wheat and rice applied as preemergence spray to soil. Six replicates are used for each treatment and for untreated controls. Measurements are taken 19 days post-treatment. At each kg/ha rate, the data of the corresponding replicates are averaged.

| Compound | Rate: kg/ha | Wheat var. Era Height in cm | Wheat var. Era Height Reduction in % | Wheat var. Garnet Height in cm | Wheat var. Garnet Height Reduction in % | Rice* var. Saturn Height in cm | Rice* var. Saturn Height Reduction in % |
|---|---|---|---|---|---|---|---|
| Control | — | 32.0 | — | 34.25 | — | 30.4 | — |

TABLE IX-continued

Evaluation of the dwarfing effect of phenylnitramines on wheat and rice applied as preemergence spray to soil. Six replicates are used for each treatment and for untreated controls. Measurements are taken 19 days post-treatment. At each kg/ha rate, the data of the corresponding replicates are averaged.

| | | Wheat | | | | Rice* | |
| --- | --- | --- | --- | --- | --- | --- | --- |
| | | var. Era | | var. Garnet | | var. Saturn | |
| Compound | Rate: kg/ha | Height in cm | Height Reduction in % | Height in cm | Height Reduction in % | Height in cm | Height Reduction in % |
| 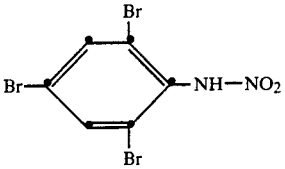 | 0.56 | 30.5 | 4.7 | 30.8 | 10.1 | 25.5 | 16.1 |
| | 1.12 | 29.5 | 7.8 | 30.5 | 10.9 | 23.6 | 23.4 |
| | 1.68 | 29.2 | 8.8 | 28.4 | 17.1 | 16.3 | 46.4 |
| | 2.24 | 28.0 | 12.5 | 27.4 | 20.0 | 16.0 | 47.4 |

*Rice at 1.68 and 2.24 kg/ha rate stand reduction (~25% and ~50%) and moderate to severe tip burn was noted.

EXAMPLE 19

Evaluation of the dwarfing effect of phenylnitramines on spring barley (var. Conquest), applied as a postemergence spray, is achieved in the following tests. Individual plants growing in 10 cm sq. pots in high porosity soil are sprayed with test solutions or suspensions, prepared as 50/50 water/acetone mixture containing 0.25% of a surfactant, when the plants are at the three-leaf to very early tillering stage. The sprayer is an overhead sprayer designed to deliver 86 gallons/acre of solution or suspension and is located about 26 cm above the plants. Plants are measured on the day of treatment and again 18 days after treatment when the dwarfing effect of the test compound is determined. During the test, all plants are fertilized with liquid fertilizer four times a day, except weekends, when they are only watered. The fertilizer is a complete one comprising 200 ppm N, 166 ppm K, 30 ppm P, plus all other essential nutrients. Data obtained 18 days after treatment are reported below.

TABLE X

| | % Dwarfing (Mean of 5 Replications) | | |
| --- | --- | --- | --- |
| Compound | 0.1 kg/hectare | 0.2 kg/hectare | 0.5 kg/hectare |
| 2,4,6-tribromo-N—nitroaniline | 13.8 | 21.3 | 37.7 |
| 2,4-dibromo-6-iodo-N—nitroaniline | — | 20.7 | 32.4 |
| 2,6-dichloro-4-iodo-N—nitroaniline | 11.8 | 15.7 | 17.4 |
| 2,6-dibromo-4-chloro-N—nitroaniline | 7.4 | 15.7 | 33.2 |
| 4-chloro-2-bromo-6-iodo-N—nitroaniline | 15.3 | 25.7 | 39.4 |
| 2-chloro-4-bromo-6-iodo-N—nitroaniline | 7.9 | 15 | 26.9 |
| 2,4-dibromo-α,α,α-trifluoro-N—nitro-o-toluidine | 26.8 | 36.2 | 50 |
| 2-chloro-4,6-dibromo-N—nitroaniline | — | 10.8 | 18.9 |
| 2-chloro-4,6-diiodo-N—nitroaniline | — | 21.5 | 21.2 |
| 2-bromo-4,6-diiodo-N—nitroaniline | — | 13 | 6.3 |
| 2,6-dibromo-3,4-dichloro-N—nitroaniline | — | — | 8.6 |

It is claimed:

1. A method for reducing relative stem growth and increasing the stiffness of stems of wheat, barley or rice comprising: applying to the locus thereof, an effective stem-growth-reducing-and-stem-stiffness-increasing amount of the compound 2, 4, 6-tribromo-N-nitroaniline.

* * * * *